United States Patent [19]

Kulshreshtha et al.

[11] Patent Number: 5,803,966
[45] Date of Patent: Sep. 8, 1998

[54] PROCESS FOR SIZING PREDNISOLONE ACETATE USING A SUPERCRITICAL FLUID ANTI-SOLVENT

[75] Inventors: Alok K. Kulshreshtha, Arlington; Garnet G. Smith, Colleyville, both of Tex.; Scott D. Anderson, Marlboro; Val J. Krukonis, Lexington, both of Mass.

[73] Assignee: Alcon Laboratories, Inc., Fort Worth, Tex.

[21] Appl. No.: 551,549

[22] Filed: Nov. 1, 1995

[51] Int. Cl.[6] .............................. G30B 7/00; A61K 9/14
[52] U.S. Cl. .............................. 117/68; 424/489; 117/925
[58] Field of Search ........................ 422/38–39; 118/300, 118/308; 117/68, 925; 424/489

[56] References Cited

U.S. PATENT DOCUMENTS

| | | | |
|---|---|---|---|
| 4,263,253 | 4/1981 | Pilz et al. ..................................... | 422/1 |
| 4,582,731 | 4/1986 | Smith ...................................... | 427/421 |
| 5,043,280 | 8/1991 | Fischer et al. ........................ | 435/235.1 |
| 5,360,478 | 11/1994 | Krukonis et al. .......................... | 117/68 |

FOREIGN PATENT DOCUMENTS

| | | |
|---|---|---|
| 90/03782 | 4/1990 | WIPO . |

OTHER PUBLICATIONS

Bodmeier et al., "Polymeric Microspheres Prepared by Spraying into Compressed Carbon Dioxide," *Pharmaceutical Research*, vol. 12(8), pp. 1211–1217, 1995.

Dixon et al., "Polymeric Materials formed by Precipitation with a Compressed Fluid Antisolvent," AIChE Journal, vol. 39(1), pp. 127–139, 1993.

Donsi et al., "Micronization by Means of Supercritical Fluids: Possibility of Application to Pharmaceutical Field," *Pharm. Acta Helv.*, vol. 66(5–6), pp. 170–173, 1991.

Gallagher et al., "Gas Antisolvent Recrystallization: New Process to Recrystallize Compounds Insoluble in Supercritical Fluids," *ACS Symposium Series 406, American Chemical Society:* Washington, D.C. pp. 334–354, 1989.

Gallagher et al., "Gas Anti–Solvent (Gas) Recrystallization: Application to Particle Design," AIChE Symposium Series, vol. 87, No. 284, pp. 96–103, 1991.

Gallagher–Wetmore et al., "Recrystallization Using Supercritical Fluids: Novel Techniques for Particle Modification," First International Particle Technology Forum, Aug. 17–19, 1994, Denver, Colorado, American Institute of Chemical Engineers.

Gallagher–Wetmore et al., "Application of Supercritical Fluids in Recrystallization: Nucleation and Gas Anti–Solvent (Gas) Techniques," *Respiratory Drug Delivery*, IV, pp. 287–295, 1994.

Larson et al., "Evaluation of Supercritical Fluid Extraction in the Pharmaceutical Industry," *Biotechnology Progress*, vol. 2(2), p. 73, 1986.

(List continued on next page.)

Primary Examiner—Raj Bawa
Attorney, Agent, or Firm—Patrick M. Ryan

[57] ABSTRACT

A process employing a supercritical fluid anti-solvent for sizing prednisolone acetate is disclosed. The process optionally incorporates sterilization filters. Average particle sizes of about 1 μm or less (number average) and narrow particle size ranges are obtainable. The process comprises the steps of (a) forming a solution by dissolving prednisolone acetate in acetone such that the concentration of prednisolone acetate is approximately 80% or less of its solubility in acetone; and (b) transporting the solution formed in step (a) through an orifice having a diameter of 50–100 μm into a mixer/expander containing compressed $CO_2$, wherein the compressed $CO_2$ is at a temperature from about 40° to 80° C. and has a density less than the density of the solution by at least 0.3 g/cc, to expand the solution so that the acetone dissolves in the $CO_2$ and the prednisolone acetate precipitates.

18 Claims, 2 Drawing Sheets

OTHER PUBLICATIONS

Mohamed et al., "Effects of Process Conditions on Crystals Obtained from Supercritical Mixtures," *AIChE Journal,* vol. 35(2), pp. 325–328, 1989.

Mulcahey et al., "Supercritical Fluid Extraction of Active Components in a Drug Formulation," *Anal. Chem.,* vol. 64, pp. 981–984, 1992.

Randolph et al., "Sub–Micron Sized Biodegradable Particles of Poly(L–Lactic Acid) via the Gas Antisolvent Spray Precipitation Process," *Biotechnology Progress,* vol. 9 (4), pp. 429–435, 1993.

Yeo et al., "Production of Microparticulate Protein Powders Using a Supercritical Fluid Anti–Solvent," *Biotech. Bioeng.,* vol. 41, pp. 341–346, 1993.

PROCESS FOR SIZING PREDNISOLONE ACETATE USING A SUPERCRITICAL FLUID ANTI-SOLVENT

FIELD OF THE INVENTION

The present invention relates to the field of pharmaceutical drug compound processing. In particular, the invention relates to a process for sizing prednisolone acetate, a water-insoluble steroidal drug compound, using a supercritical fluid anti-solvent.

BACKGROUND OF THE INVENTION

It is generally accepted that particle sizes in ophthalmic suspensions should be less than 10 $\mu$m in order to minimize irritation. Small drug particle sizes in pharmaceutical suspensions are desirable for a number of other reasons as well, including enhanced bioavailability. Additionally, in comparison with suspensions of particles of larger sizes, suspensions of particles of about 1 $\mu$m or less possess superior particulate stability due to the colloidal nature of the smaller particles.

Conventional drug sizing techniques have known limitations. For example, spray drying processes, which typically use heated gases, are generally not suitable for heat-labile compounds and provide low yields; wet roller ball milling is not very efficient and it is difficult to separate and recover the sizing beads from the milled slurry; and micronization is not suitable for soft powders. Additionally, in controlled precipitation and lyophilization processes, particle sizes are difficult to control.

Efforts have recently been made to use supercritical fluids in drug sizing. G. Donsi and E. Reverchon ("Micronization by Means of Supercritical Fluids: Possibility of Application to Pharmaceutical Fields," Pharm. Acta Helv., 66 (5–6), pp. 170–173, 1991) have summarized initial efforts by a number of people who have attempted to apply supercritical fluid micronization to pharmaceutical drug compounds. One advantage of using supercritical fluid processing to size drug compounds is its applicability to heat-labile drugs. Supercritical fluids are used to size drugs in the following way. First, the pharmaceutical drug compound is dissolved in a compressed fluid under supercritical temperature and pressure conditions. Then, the resulting solution is rapidly expanded by dramatically decreasing the pressure. The solvent power of the supercritical fluid dramatically decreases as the pressure is let down, causing the drug compound to precipitate. The resulting particle size and particle size distribution from this process depend on supercritical fluid feed rates, upstream temperature and pressure, and downstream temperature and pressure.

U.S. Pat. No. 4,582,731 (Smith) discloses a supercritical fluid injection molecular spray process (FIMS) for depositing films or forming fine powders. The FIMS process utilizes a fluid injection technique which calls for rapidly expanding a supercritical solution through a short orifice into a relatively lower pressure region. The solute nucleation and growth phenomena during expansions may be influenced by spray operating parameters such as solute concentration, nozzle size and rate of pressure drop. See, for example, Mohamed, et al., "Effect of Process Conditions on Crystals Obtained from Supercritical Mixtures," AIChEJ, 35, 325 (1989).

In order to take advantage of micronization by means of supercritical fluids, the drug compound must be soluble in a supercritical fluid, such as carbon dioxide. Although the solvent power of supercritical fluids may be adjusted over a wide range of operating conditions, and can even be enhanced, in some cases, by the addition of cosolvents or entrainers, some pharmaceutical compounds remain insoluble or only slightly soluble in supercritical solvents.

Gallagher et al., "Gas Antisolvent Recrystallization: New Process to Recrystallize Compounds Insoluble in Supercritical Fluids," Amer. Chem. Soc. Symp. Ser., No. 406 (1989), disclose a process in which $CO_2$ is bubbled as an antisolvent into a liquid organic solvent containing dissolved nitroguanidine to precipitate nitroguanidine crystals. After the crystals have been recovered from the liquid solvent/antisolvent solution, the solvent and antisolvent solution can be separated by simple pressure changes. Gallagher et al. also disclose that the rate of addition of a gas antisolvent can control particle size, size distribution and shape. Although their experiments were directed to a specific explosive, nitroguanidine, Gallagher et al. suggest that the process is quite general in its capabilities of recrystallizing virtually any solid material provided that the solid is soluble in some organic liquid and that some gas is sufficiently soluble in the liquid to expand it appreciably. See also, Gallagher et al., AIChEJ, vol. 87, 96–103 (1991), based on a presentation made at the 1990 AIChE Annual Meeting in Chicago, Ill., disclosing the applicability of the gas anti-solvent process to other compounds including steroids.

In a separate communication, "Application of Supercritical Fluids in Recrystallization: Nucleation and Gas Anti-Solvent (GAS) Techniques," Respiratory Drug Delivery IV, pp. 287–295 (1994), Gallagher et al. have sized certain steroidal drug compounds. A supercritical fluid nucleation technique, which does not employ an anti-solvent, was used to size prednisolone. The average particle size of the recrystallized prednisolone was found to decrease with increasing drug/solvent solution pressure. The majority of the recrystallized prednisolone formed with the supercritical fluid at a pressure of 5000 psi and temperature of 120 C appeared as loose agglomerates of 1 $\mu$m or less primary particles (as measured by calibrated light microscopy). Dexamethasone was sized using a gas anti-solvent technique rather than the nucleation technique, because the solubility of dexamethasone in $CO_2$ is low.

WO 90/03782 (Schmitt) discloses a process for producing finely divided solids, including steroids, which comprises (1) dissolving the solid to be finely divided in a liquid carrier solvent to form an injection solution and (2) adding the injection solution to a volume of anti-solvent sufficient to precipitate or crystallize the solid. This reference also discloses the addition of a sterilizing filter to sterilize and size compounds in a single process. The reference defines the operable solids capable of being finely divided in the claimed process as any solid material which needs to be sub-divided in the solid state and which can be dissolved in some liquid carrier solvent. The solid is preferably a steroid, benzodiazepene, penicillin, or cephalosporin. Particle size is controlled by adjusting the solution/anti-solvent contact time. The only experimental examples relate to triamcinolone acetonide, for which the particle sizes obtained are of the order of 5–10 $\mu$m, as measured by calibrated light microscopy.

U.S. Pat. No. 5,360,478 (Krukonis et al.) discloses a gas anti-solvent recrystallization process capable of producing void-free crystals of certain materials. This reference emphasizes the advantages of employing gas anti-solvents rather than liquid anti-solvents, and describes the gas anti-solvent process as applicable to organic and inorganic materials. Particle size and particle size distribution are determined by a variety of factors including the rate of supersaturation and the manner of anti-solvent addition.

Despite the disclosures by the references mentioned above, there is a need for an improved processes for sizing prednisolone acetate, which is capable of producing a number average particle size of about 1 µm or less and a particle size distribution having no particles greater than 10 µm (based on number distribution).

SUMMARY OF THE INVENTION

The present invention provides a process for sizing prednisolone acetate which produces number average particle sizes of 1 µm or less, a particle size distribution having no particles greater than 10 µm (based on number distribution), and a particle size distribution index of less than 4. The process comprises the steps of:

(a) forming a solution by dissolving prednisolone acetate in acetone; and (b) transporting the solution through an orifice into a mixer/expander containing compressed $CO_2$, wherein the compressed $CO_2$ is at a temperature from about 40° to 80° C. and has a density less than the density of the solution by at least 0.3 g/cc, to expand the solution so that the acetone dissolves in the $CO_2$ and the prednisolone acetate precipitates.

In a preferred embodiment, a sterilizing filter is also incorporated to provide a single process for sterilizing and sizing steroidal drug compounds. This preferred method comprises the steps of:

(a) forming a solution by dissolving prednisolone acetate in acetone; and (b) sterilizing the solution by transporting the solution through a sterilizing filter to remove bacteria and other impurities; and (c) transporting the sterilized solution through an orifice into a mixer/expander containing sterile compressed $CO_2$, wherein the compressed $CO_2$ is at a temperature from about 40° to 80° C. and has a density less than the density of the solution by at least 0.3 g/cc, to expand the solution so that the acetone dissolves in the $CO_2$ and the prednisolone acetate precipitates.

Among other factors, the present invention is based on the finding that small particle sizes are achieved by selecting parameters so that the density of the solution containing the drug is greater than the density of the compressed fluid anti-solvent.

DETAILED DESCRIPTION OF THE INVENTION

Figure 1:
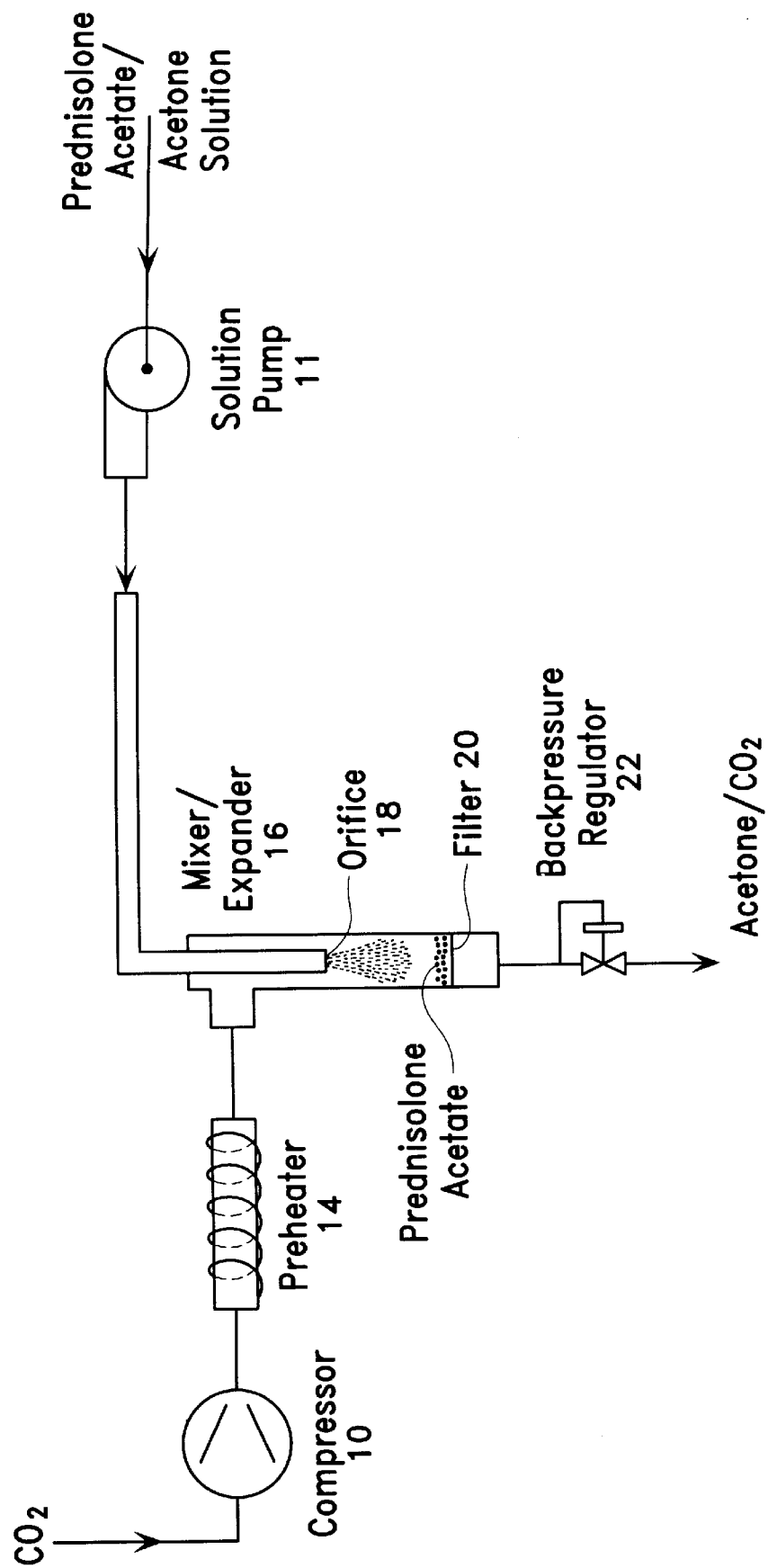
FIG. 1 is a schematic diagram of an embodiment of the sizing process of the present invention.

"Weight average particle size" means $\Sigma(n_i d_i^4)/\Sigma(n_i d_i^3)$; where $n_i$ is the number of particles in a specified particle diameter range, and $d_i$ is the mid-point of the specified particle diameter range.

"Number average particle size" means $\Sigma(n_i d_i)/\Sigma(n_i)$; where $n_i$ and $d_i$ have the same meanings as above.

"Particle size distribution index" means the ratio of weight average particle size to number average particle size.

Prednisolone acetate is a known compound and is commercially obtainable. Typically, the commercially available prednisolone acetate consists of particles larger than desirable for ophthalmic applications. The process of the present invention sizes the prednisolone acetate such that number average particle sizes of 1 µm or less are obtained. The particle size distribution is narrow, with no particles greater than 10 µm (based on number distribution), and the particle size distribution index for the prednisolone acetate sized according to the process of the present invention is less than 4. In a preferred embodiment, the process of the present invention produces average particle sizes of 0.5 µm or less with no particles greater than about 5 µm.

The process of the present invention can be described with reference to the following steps: (a) forming a solution of the prednisolone acetate to be sized by dissolving it in acetone, and (b) sizing the prednisolone acetate by transporting the solution through an orifice into a mixer/expander, which contains compressed $CO_2$, wherein the compressed $CO_2$ is at a temperature from about 40° to 80° C. and has a density less than the density of the solution by at least 0.3 g/cc, to expand the solution so that the acetone dissolves in the $CO_2$ and the prednisolone acetate precipitates.

Forming a solution

Prednisolone acetate is dissolved in commercially available acetone. In order to avoid any undesirable saturation effects, the prednisolone acetate concentration in the prednisolone acetate/acetone solution should be approximately 80% of its solubility in acetone. Under the preferred conditions indicated below, the prednisolone acetate concentration in the solution is preferably from about 0.5 to 0.6% (w/v), and most preferably from about 0.52 to about 0.55% (w/v).

The prednisolone acetate/acetone solution is preferably at approximately room temperature when it is injected into a mixer/expander chamber, where it is combined with the compressed $CO_2$. At room temperature, acetone has a density of about 0.79 g/cc.

Sizing the prednisolone acetate

The prednisolone acetate/acetone solution formed above is injected through an orifice into a suitable mixer/expander where it is combined with the anti-solvent, compressed $CO_2$. The orifice may be a spray nozzle or a laser-drilled orifice. The orifice is preferably a laser-drilled orifice having a diameter size from 50–100 µm.

The mixer/expander may be various shapes and sizes and can be readily fabricated commercially. The mixer/expander should have appropriate temperature and pressure ratings for the compressed $CO_2$, and allow adequate mixing of the $CO_2$ and the prednisolone acetate/acetone solution. A filter, for example a nylon filter, is conveniently inserted in the mixer/expander to trap the precipitated prednisolone acetate. A preferred design for the mixer/expander is that shown for the mixer/expander in FIG. 1.

The temperature of the compressed $CO_2$ entering the mixer/expander, should be from about 40° to 80° C. The $CO_2$ temperature is preferably from about 45° to 65° C., and is most preferably about 60° C. The $CO_2$ should be compressed to a pressure sufficient to cause the $CO_2$ anti-solvent to have a density less than that of the acetone solvent by at least 0.3 g/cc. Preferably, the $CO_2$ is compressed to a pressure sufficient to cause the $CO_2$ to have a density from about 0.30 to 0.41 g/cc.

The flow rate of the prednisolone acetate/acetone solution entering the orifice is preferably from about 2 to 4 ml/min., more preferably from about 2.5 to 3.0 ml/min. The preferred flow rate of the compressed $CO_2$ entering the mixer/expander is preferably from about 50 to 80 standard liters/ min. More preferably, the $CO_2$ flow rate entering the mixer/expander is about 60 standard liters/min. (approximately 108 g/min.).

While those skilled in the art will readily appreciate that alternative apparatus designs are possible, a preferred design for the sizing process of the present invention is shown in FIG. 1. With reference to FIG. 1, commercially available $CO_2$ is fed to the mixer/expander (16) through compressor (10) and preheater (14). The desired pressure of the $CO_2$ entering the mixer/expander is controlled using the compressor (10) and the backpressure regulator (22). The desired temperature of the $CO_2$ entering the mixer/expander is controlled using the preheater (14). A solution of is prednisolone acetate (PA) in acetone is fed via a solution pump (11) to the mixer/expander (16) through an orifice (18) where it comes in contact with the $CO_2$, which is at supercritical conditions. Upon contact, the $CO_2$ expands the PA/acetone solution whereby the acetone dissolves in the $CO_2$ and the PA precipitates. The precipitated PA is collected on a filter (20). The acetone/$CO_2$ mixture exits mixer/expander (16) and is optionally separated in order to recover acetone prior to venting or recycling $CO_2$.

Sterilizing the Drug

The process of the present invention may optionally be adapted to sterilize as well as size the prednisolone acetate. Sterilization may be accomplished by transporting the prednisolone acetate/acetone solution and compressed $CO_2$ through sterilizing filters prior to introducing them into the mixer/expander. The sterilizing filters should be of the size specified by the U.S. Food and Drug Administration (FDA) for aseptic sterilization. Currently, solutions passed through a filter having pores no larger than 0.22 μm are considered sterile by the FDA. The prednisolone acetate/acetone solution sterilizing filter is preferably positioned downstream of any solution pump and upstream of the orifice. The $CO_2$ sterilizing filter is preferably inserted downstream of any compressor but upstream of the mixer/expander. The lines transporting the sterilized $CO_2$, and prednisolone acetate/acetone solution, and mixtures of the two, are preferably stainless steel (316L).

Figure 2:
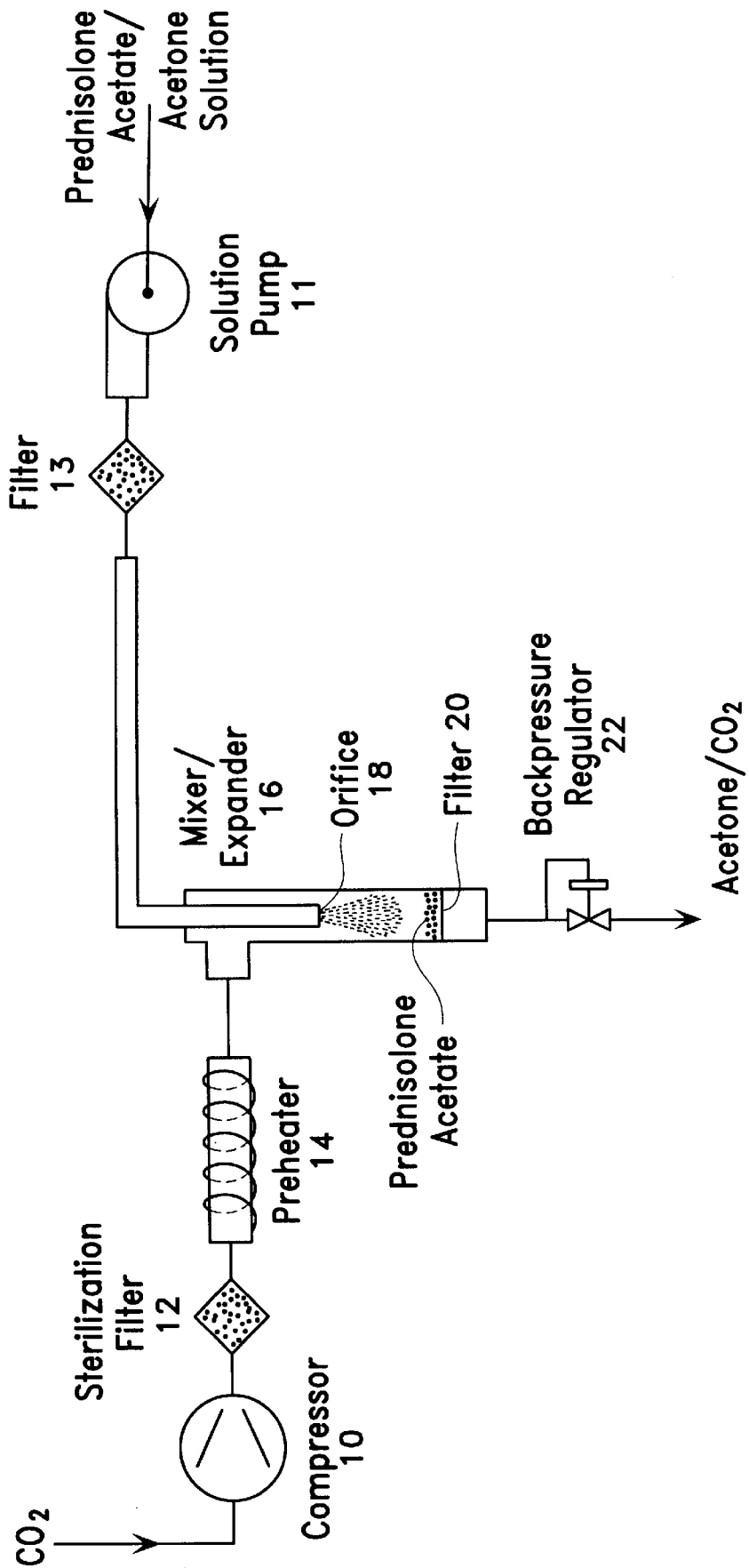
FIG. 2 is a schematic diagram of an embodiment of the sizing and sterilization process of the present invention.

A preferred embodiment of the single process for both sterilizing and sizing prednisolone acetate according to the present invention is shown in FIG. 2.

The following examples are intended to illustrate, but in no way limit, the present invention.

EXAMPLES

Prednisolone acetate obtained from Roussel Corporation (New York, N.Y.) was sized under various operating conditions using the apparatus design shown in FIG. 1.

Example 1

Using the apparatus design shown in FIG. 1, the particle sizing was carried out in the following manner. A solution of prednisolone acetate in acetone (1.55 g of prednisolone acetate in 300 ml acetone) was pumped at a rate of 3.0 ml/min to the orifice that was situated in the mixer/expander. Compressed $CO_2$ was supplied to the mixer/expander at a rate of 60 standard liters per minute. The pressure of the $CO_2$ in the mixer/expander was controlled by a back-pressure regulator. The particles of prednisolone acetate formed during the dissolution of acetone in the $CO_2$ (and concurrently the dissolution of $CO_2$ in the acetone) were collected on a filter situated at the outlet of the mixer/expander. The $CO_2$/acetone solution coming out of mixer/expander was expanded to ambient to separate acetone from the solution. At the end of the test the mixer/expander was disassembled and the prednisolone acetate particles were recovered for particle size analysis. An amount of approximately 0.5 g of processed prednisolone acetate was recovered. A Microtrac® X100 (from Leeds+ Northrup, St. Petersburg, Fla.) particle size analyzer was used to measure the particle size distribution of the processed prednisolone acetate in an aqueous menstruum containing polysorbate 80 and benzalkonium chloride. The number average particle size was calculated using the Microtrac® X100 in built software. For the particle size distribution measurements, the prednisolone acetate particles were assumed to be transparent spherical and the refractive indices of the particles and the menstruum were 1.59 and 1.33, respectively. The average number is particle size of the processed prednisolone acetate was 0.45 μm with a particle size distribution index of 3.49.

Examples 2–7

Examples 2–7 were conducted in the same way as Example 1, with the respective operating parameters indicated in Table 1. Example 7 was carried out under the same conditions as Example 2, except that Example 7 was a scaled-up run in which approximately 10 g of the processed prednisolone acetate was recovered. The results from all of the Examples are shown in Table 1 below.

TABLE 1

| Example No. | $CO_2$ Pressure | $CO_2$ Temperature | $CO_2$ Density | Avg. Particle Size (weight basis) | Avg. Particle Size (number basis) | Number Range | MW/MN* |
| --- | --- | --- | --- | --- | --- | --- | --- |
| 1 | 100 | 60 | 0.30 | 1.58 | 0.45 | 0.24–3.89 | 3.49 |
| 2 | 100 | 60 | 0.30 | 1.16 | 0.45 | 0.29–1.94 | 2.56 |
| 3 | 100 | 55 | 0.34 | 1.12 | 0.45 | 0.29–3.89 | 2.47 |
| 4 | 100 | 100 | 0.19 | 11.32 | 3.17 | 1.63–31.11 | 3.56 |
| 5 | 200 | 40 | 0.84 | 23.07 | 6.33 | 3.27–62.33 | 3.64 |
| 6 | 200 | 120 | 0.41 | 6.55 | 0.20 | 0.14–4.62 | 32.75 |
| 7 | 100 | 60 | 0.30 | 1.645 | 0.47 | 0.29–3.89 | 3.53 |

*MW/MN = Particle Size Distribution Index

The results shown in Table 1 demonstrate that prednisolone acetate sizing processes according to the present invention (Examples 1,2,3 and 7) produce average particle sizes of about 1 μm or less, a narrow particle size distribution with no particles greater than about 10 μm, and a particle size index of less than 4.

We claim:

1. A process for sizing prednisolone acetate which produces a number average particle size of 1 μm or less, a particle see distribution having no particles greater than 10 μm (based on number distribution), and a particle size distribution index of less than 4, wherein the process comprises the steps of:

(a) forming a solution by dissolving prednisolone acetate in acetone so that the concentration of prednisolone acetate in the solution is approximately 80% or less of its solubility in acetone; and (b) transporting the solution formed in step (a) through an orifice having a diameter of 50–100 μm into a mixer/expander containing compressed $CO_2$, wherein the compressed $CO_2$ is at a temperature from about 40° to 80° C. and has a density less than the density of the solution by at least 0.3 g/cc, wherein the solution is expanded so that the acetone dissolves in the $CO_2$ and the prednisolone acetate precipitates.

2. The process of claim 1 wherein the process produces prednisolone acetate having a number average particle size of 0.5 μm or less and a particle size distribution having no particles greater than 5 μm (based on number distribution).

3. The process of claim 1 wherein the prednisolone acetate concentration in the solution formed in step (a) is from about 0.5 to 0.6% (w/v).

4. The process of claim 3 wherein the prednisolone acetate concentration in the solution formed in step (a) is from about 0.52 to 0.55% (w/v).

5. The process of claim 1 wherein the temperature of the compressed $CO_2$ is from about 45° to 65° C.

6. The process of claim 1 wherein the temperature of the compressed $CO_2$ is about 60° C.

7. The process of claim 1 wherein the compressed $CO_2$ has a density from about 0.30 to 0.41 g/cc.

8. The process of claim 1 wherein the solution enters the orifice at a flow rate from about 2 to 4 ml/min. and the compressed $CO_2$ enters the mixer/expander at a flow rate from about 50 to 80 standard liters/min.

9. The process of claim 8 wherein the solution enters the orifice at a flow rate from about 2.5 to 3.0 ml/min. and the compressed $CO_2$ enters the mixer/expander at a flow rate of about 60 standard liters/min.

10. A process for sterilizing and sizing prednisolone acetate which produces a number average particle size of 1 μm or less, a particle size distribution having no particles greater than 10 μm (based on number distribution), and a particle size distribution index of less than 4, wherein the process comprises the steps of:

(a) forming a solution by dissolving prednisolone acetate in acetone so that the concentration of prednisolone acetate in the solution is approximately 80% or less of its solubility in acetone;

(b) sterilizing the solution formed in step (a) by transporting it through a sterilizing filter to remove bacteria and other impurities; and (c) transporting the sterilized solution formed in step (b) through an orifice having a diameter of 50–100 μm into a mixer/expander containing sterile compressed $CO_2$, wherein the compressed $CO_2$ is at a temperature from about 40° to 80° C. and has a density less than the density of the solution by at least 0.3 g/cc, wherein the solution is expanded so that the acetone dissolves in the $CO_2$ and the prednisolone acetate precipitates.

11. The process of claim 10 wherein the process produces prednisolone acetate having number average particle size of 0.5 μm or less and a particle size distribution having no particles greater than 5 μm (based on number distribution).

12. The process of claim 10 wherein the prednisolone acetate concentration in the solution formed in step (a) is from about 0.5 to 0.6% (w/v).

13. The process of claim 12 wherein the prednisolone acetate concentration in the solution formed in step (a) is from about 0.52 to 0.55% (w/v).

14. The process of claim 10 wherein the temperature of the compressed $CO_2$ is from about 45° to 65° C.

15. The process of claim 10 wherein the temperature of the compressed $CO_2$ is about 60° C.

16. The process of claim 1 wherein the compressed $CO_2$ has a density from about 0.30 to 0.41 g/cc.

17. The process of claim 1 wherein the solution enters the orifice at a flow rate from about 2 to 4 ml/min. and the compressed $CO_2$ enters the mixer/expander at a flow rate from about 50 to 80 standard liters/min.

18. The process of claim 17 wherein the solution enters the orifice at a flow rate from about 2.5 to 3.0 ml/min. and the compressed $CO_2$ enters the mixer/expander at a flow rate of about 60 standard liters/min.

* * * * *